United States Patent [19]

Reischl et al.

[11] Patent Number: 5,683,658
[45] Date of Patent: Nov. 4, 1997

[54] REAGENT BOTTLE

[75] Inventors: Franz Reischl; Taghi Noormofidi; Erich Kleinhappl, all of Graz, Austria

[73] Assignee: AVL Medical Instruments AG, Schaffhausen, Switzerland

[21] Appl. No.: 670,433

[22] Filed: Jun. 26, 1996

[30] Foreign Application Priority Data

Jul. 14, 1995 [AT] Austria ................... 1203/95

[51] Int. Cl.⁶ .................. B01L 3/00; G01N 37/00
[52] U.S. Cl. ............... 422/102; 422/63; 422/100; 422/103; 436/43; 436/180; 73/863.85; 73/864.74; 73/864.85; 73/864.86; 215/234; 215/378; 220/89.2; 220/367.1; 220/601
[58] Field of Search .............. 422/63, 67, 49, 422/100, 102, 103; 436/43, 174, 179, 180; 206/459.1; 215/40, 250, 251, 257, 234, 378; 220/89.2, 367.1, 601; 73/864.22, 863.85, 864.74, 864.85, 864.86

[56] References Cited

U.S. PATENT DOCUMENTS

| | | | |
|---|---|---|---|
| 4,243,150 | 1/1981 | Gunne et al. | 215/247 |
| 4,381,776 | 5/1983 | Latham, Jr. | 604/317 |
| 4,844,870 | 7/1989 | Rasmussen et al. | 422/68 |
| 5,027,872 | 7/1991 | Taylor et al. | 141/347 |
| 5,125,522 | 6/1992 | Pezzoli et al. | 215/250 |
| 5,143,236 | 9/1992 | Gueret | 215/311 |
| 5,171,538 | 12/1992 | Tremmel et al. | 422/100 |
| 5,213,967 | 5/1993 | Erdman et al. | 435/31 |
| 5,417,121 | 5/1995 | Andersen et al. | 73/864.22 |
| 5,419,316 | 5/1995 | Bernstein | 128/203.12 |
| 5,472,112 | 12/1995 | Maciejewski | 220/745 |

FOREIGN PATENT DOCUMENTS 2166571 9/1974 Germany.
3938559 5/1991 Germany.

*Primary Examiner*—Long V. Le
*Attorney, Agent, or Firm*—Watson Cole Stevens Davis, P.L.L.C.

[57] ABSTRACT

A reagent bottle suitable for insertion into a sample analyzer features a sample discharge opening plugged by an elastic, pierceable stopper, and an air inlet. Both the sample discharge opening and the air inlet are located on the same side of the reagent bottle, the axes of the two openings running parallel to each other, such that both openings can be docked onto corresponding sampling and air inlet elements of the analyzer in one and the same working process when the reagent bottle is inserted into the analyzer. The elastic stopper is covered on its outside by a protective foil and has a recess at a puncturing site enabling the sampling element to puncture the foil more easily. Bordering on the recess of the stopper is an area which is prepunctured but offers a tight elastic seal.

15 Claims, 4 Drawing Sheets

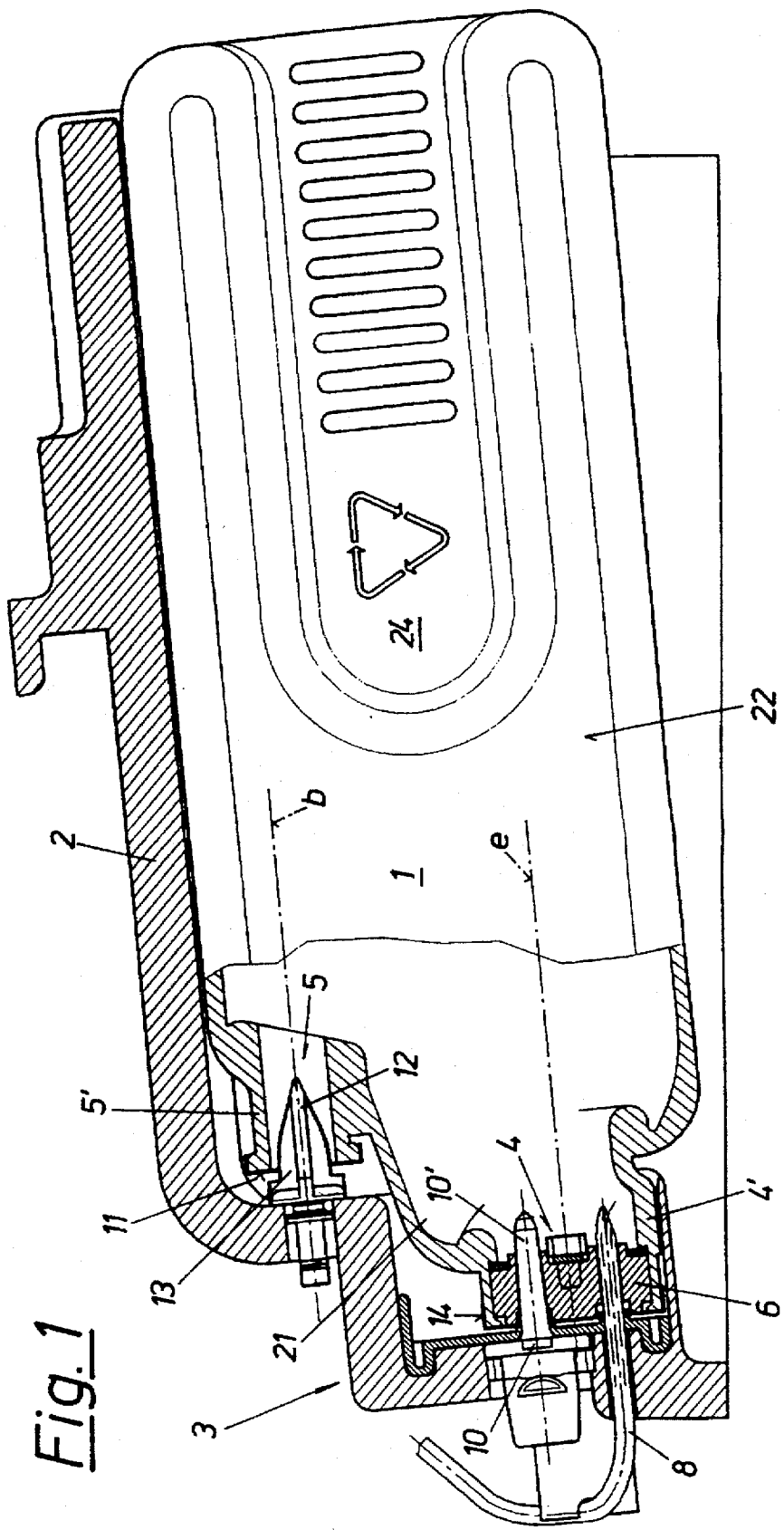

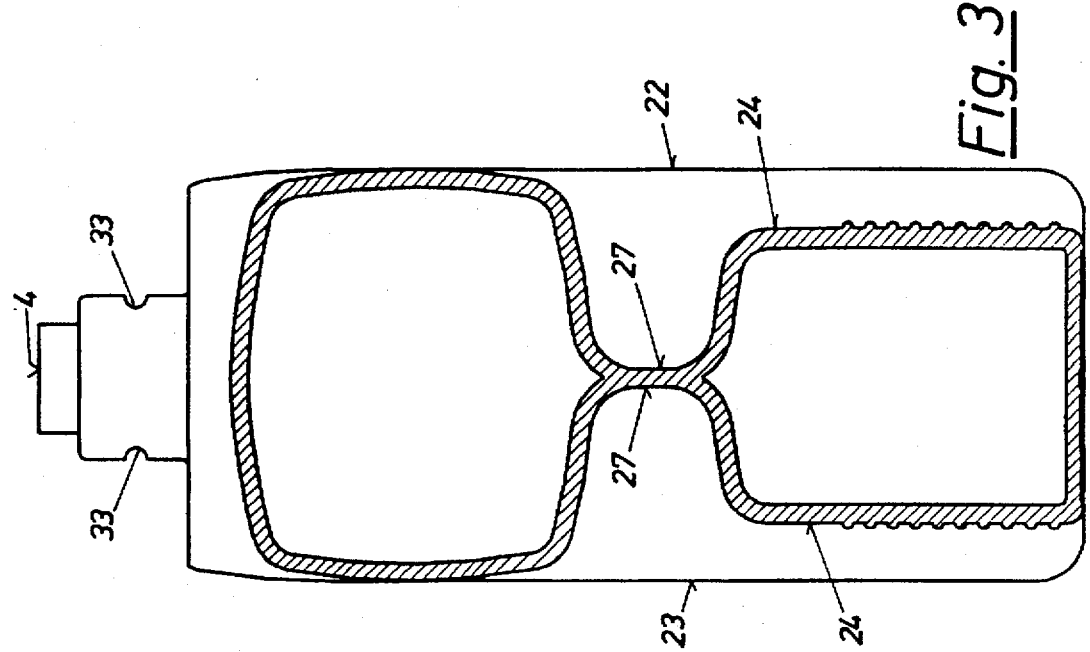
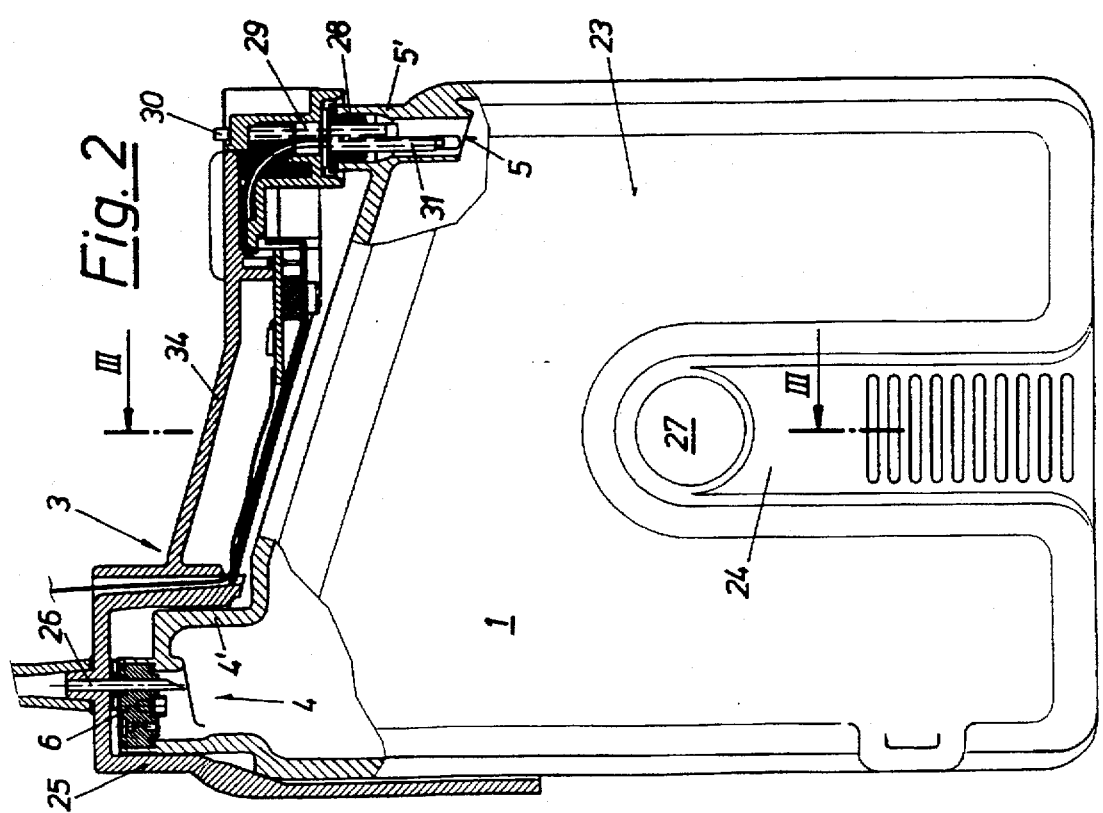

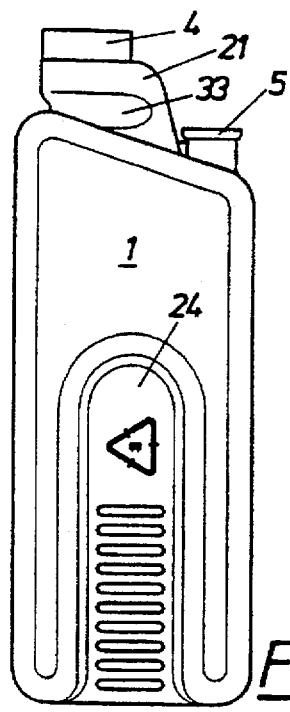
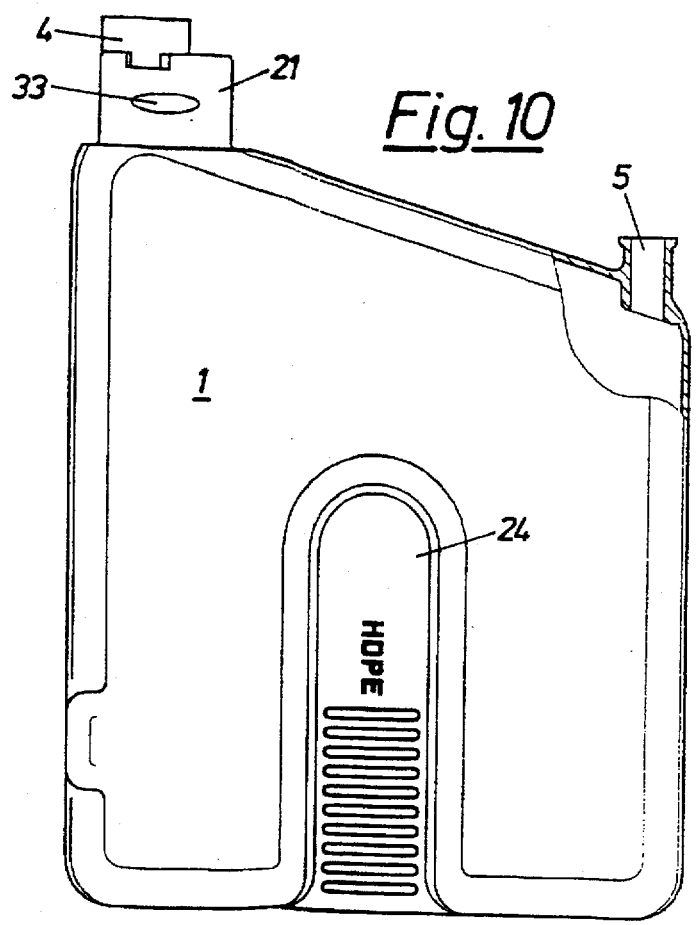
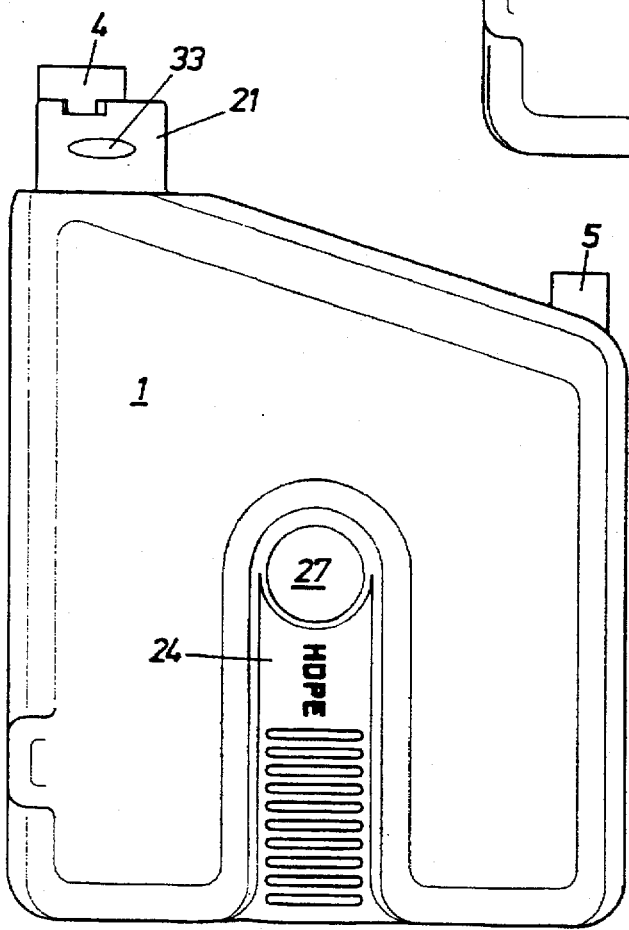
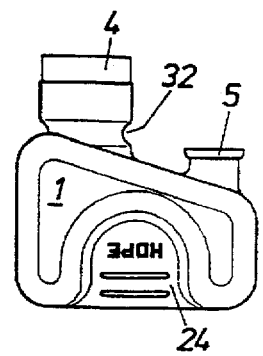

REAGENT BOTTLE

BACKGROUND OF THE INVENTION

The present invention relates to a reagent bottle suitable for insertion into a sample analyzer, with a sample discharger opening plugged by an elastic, pierceable stopper, and an air inlet, which elastic stopper is covered on its outside by a protective foil and is provided with a recess at a puncturing site enabling a sampling element of the analyzer to puncture the foil more easily.

DESCRIPTION OF THE PRIOR ART

Sample analyzers for assaying samples in an environmental, medical or technological context usually; require a number of reagent bottles supplying the analyzer with calibrating, control or washing solutions. In most cases several different bottles with different calibrating solutions are provided, which must be docked onto sampling elements in a corresponding receiving part of the analyzer. Such analyzers further require waste containers receiving the processed sample at the end of tile measuring process as well as the used-up reagent, control and washing media.

Commercially available reagent bottles are the flat plastic bottles with substantially plane side-faces and rectangular cross-section described in DE-39 38 559 A1, for example. On the narrow front face of the reagent bottle a sample discharge opening is located near the bottom, which is closed by an elastic, pierceable stopper. This stopper is covered by a protective foil that may also be pierced. On the top face of the reagent bottle an air inlet is provided, which remains closed by a screw-cap before the bottle is inserted into the analyzer. Inserting the bottle into the analyzer takes a certain manipulating effort as the sample discharge opening has to be connected to the sampling element of the analyzer, and the air inlet has to be opened and connected to corresponding docking elements of the analyzer.

In DE-21 66 571 a reagent bottle is disclosed whose air inlet is located on the same side of the bottle as the sample discharge opening, the axes of the two openings extending in parallel. But even in that case some manipulations are necessary to connect the bottle to an analyzer, such as removing a connecting tube between the two openings.

SUMMARY OF THE INVENTION

It is an object of the present invention to propose a reagent bottle for use in a sample analyzer which can be inserted into the apparatus in a simple manner, and with a minimum of handling.

In the invention this object is achieved by proposing that an area be provided bordering on the recess of the stoppers, which is prepunctured yet sealing tightly and elastically, and that the sample discharge opening and the air inlet both be located on the same side of the reagent bottle, the axes of the two openings running parallel to each other, and further that both openings dock onto suitable air inlet and sampling elements of the analyzer in one and the same working process when the reagent bottle is inserted into tile analyzer. During this process the cover foils of the two openings are punctured by the air inlet and sampling elements, and a connection to the analyzer is established. Prepuncturing the stopper will considerably reduce the force needed for the sampling element to pierce the stopper, thus permitting even relatively blunt sampling elements to be used in the sample analyzer. This will eliminate the danger of injuries for the user during cleaning work in the area of the puncturing needle.

The elastic stopper may be made of an elastomer, such as silicone, EPDM or the like, and sealed with an aluminium/PE foil. The sealing process serves to bead the rim of the bottleneck, thus ensuring that the elastomer stopper will remain in the bottle, and also as permeation barrier and quality seal. In this way the user will recognize whether the bottle is intact.

Another disadvantage of conventional reagent bottles is that the level of the reagent contained in the bottle in usually read by marks on the outside of the bottle. This will require continuous checking of these marks, however.

For this reason it is provided in further development of the invention that the elastic stopper be pierceable at a second site located above the sampling tube in the inserted position of the reagent bottle, by an element measuring the filling level, the puncturing site also hating a recess and a prepunctured area. The element measuring the filling level in-ill transmit its signals to the evaluation unit of the analyzer; once the level has dropped below a certain mark, the user is either alerted by respective signals to exchange the reagent bottle or otherwise informed how any measurements will be possible before the bottle has to be exchanged.

In an enhanced variant of the invention the conical sealing faces adjoin the prepunctured area or areas on the inside of the stopper. Unlike in the design described in DE-39 38 559 A1 where uncontrolled cracks will occur when the elastomer is punctured by the point of a needle and a perfect seal can no longer be guaranteed, the conical sealing faces adjacent to the prepunctured areas will produce a seal that is absolutely tight in the inserted state, as the conical areas will perfectly conform to a sampling element or an element for measurement of the filling level.

When the reagent bottle is inserted into the analyzer the air inlet is pierced by a puncturing pin provided in the apparatus, and, at the sample discharge opening, the protective foil and the prepunctured stopper are pierced one after the other by a level sensor and a sampling tube.

To protect the stopper from unduly bending during piercing, it is provided with a supporting plate on its inside, which rests against a projection on the neck of the bottle and has openings in the area of the two puncturing sites.

It is proposed in a variant of the invention that a light-guiding rod for measuring the filling level be provided to pierce the second puncturing site, the neck of the sample discharge opening exhibiting an enlargement, at least in the area situated near the top in the inserted state, inhere air bubbles may be received, which would otherwise interfere with the optical measurement.

For better handling the reagent bottle should be provided with a recessed grip on either of two opposite side-faces, which will reduce the cross-section of the bottle in the recessed area and increase the stability of the reagent bottle.

Another advantage of this invention is that the reagent bottle can be used in the analyzer as a waste bottle after having been emptied, the elastic stopper of the sample discharge opening receiving the connecting line of a vacuum primp, and the air inlet receiving a unit comprising a feed line and an element for measuring the filling level of tile bottle.

As the reagent bottle must be able to withstand the forces of a slight vacuum during its use as a waste container, it will be an advantage for the bottle to haste depressions approximately in the middle of two opposite side-faces, in order to stabilize the two sides relative to each other. According to the invention the two depressions could be located in the area of the recessed grips.

Finally, it is provided by the invention that the neck of the sample discharge opening have a continuous annular groove running along its outside, or at least too opposite dents, for the purpose of holding the reagent bottle in a filling plant.

BRIEF DESCRIPTION OF THE DRAWINGS

The invention still be further described with reference to the accompanying drawings, in which FIG. 1 shows a reagent bottle of the invention, which is inserted in a sample analyzer, in a partial section, FIG. 2 shows a variant of the reagent bottle of the invention in a sectional view corresponding to FIG. 1, FIG. 3 shoes a section of a reagent bottle along line III—III in FIG. 2.

DETAILED DESCRIPTION OF PREFERRED EMBODIMENTS

Figure 4:
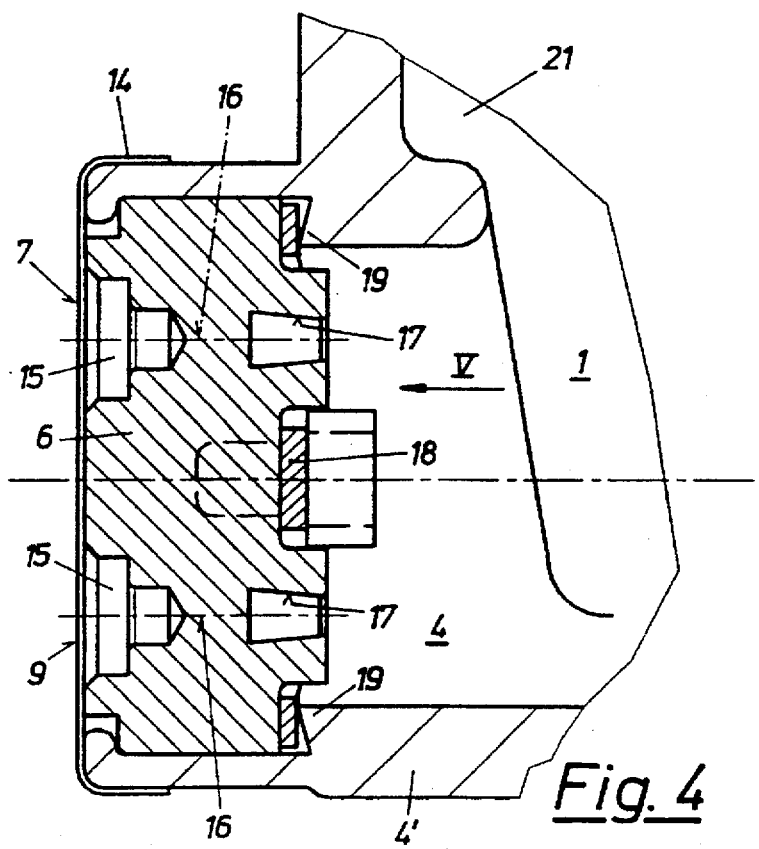
FIG. 4 shows an elastic, pierceable stopper of the reagent bottle of FIG. 1, in an enlarged view.

The reagent bottle 1 shown in FIG. 1 is inserted into the receiving part 2 of a sample analyzer 3 not shown here in detail. The reagent bottle 1 has a sample discharge opening 4 and an air inlet 5 on one and the same side, each of which openings is located in a neck-shaped part 4', 5' of the reagent bottle 1. The two axes e and b of the sample discharge opening 4 and the air inlet 5 run parallel to each other and form an acute angle with the horizontal plane, such that the reagent bottle 1 in its inserted state has a sample discharge opening 4 that is inclined downwards permitting the bottle to be drained almost completely.

The reagent bottle 1 is inserted into the receiving part 2 of the sample analyzer 3 by a simple linear sliding movement along axes e and b. At the same time, corresponding sampling and air inlet elements 8, 13 of the analyzer are inserted into the two openings 4, 5 in one and the same working process.

The sample discharge opening 4 is plugged by art elastic stopper 6, which at a first site 7 is pierced by sampling tube 8 of the analyzer, and at a second site 9 by art element 10 measuring the liquid level in the bottle. In the example shown in this draining, the element used for level measuring is a light-guiding rod 10'.

As an alternative, other elements of a know type could be used for this purpose, such, as conductivity measuring electrodes.

Before the reagent bottle 1 containing a calibrating, control, or washing solution is inserted, the air inlet 5 is covered by a foil 11, which is pierced upon insertion by a puncturing pin 13 provided with several ribs 12.

The elastic stopper 6 also is covered by a protective foil 14, which covers the upper portion of the neck 4' of the sample discharge opening 4 as well. This detail is shown more clearly in FIG. 4, where it can also been seen that recesses lo are provided at the two puncturing sites 7 and 9 for easier puncturing of the foil 14. The two recesses 15 are followed by prepunctured areas 16, which are prepunctured by a pointed pin (diameter 1 to 2 mm) while the stopper 6 is inserted into the sample discharge opening 4. Due to the elasticity of the stopper, these areas remain absolutely tight, however, while facilitating passage of the sampling tube 8 and the light-guide 10 during insertion of the reagent bottle 1 into the analyzer. On the inside of the stopper 6 conical sealing faces 17 are adjacent to the areas 16, which closely surround the sampling tube 8 and the light-guiding rod 10'.

To better support the load arising from piercing the stopper, the stopper 6 is provided with a supporting plate 18 or its inside, which rests against a projection 19 of the neck 4'. In the area of the two puncturing sites 7 arid 9, the supporting plate 18 has openings 20, which are passed through by the light-guiding rod 10' and the sampling tube 8 when the reagent bottle 1 is put into the analyzer.

Figure 6:
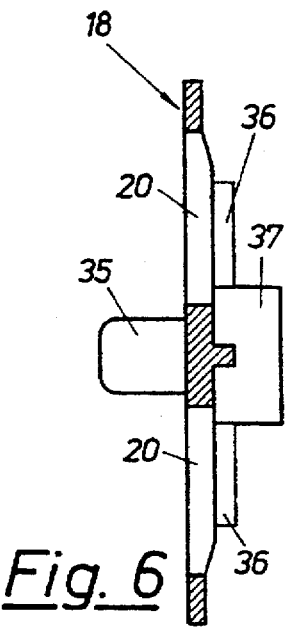
FIGS. 5 to 7 show different views and sections of a supporting plate of the elastic stopper of FIG. 4, FIGS. 9 to 11 show a set of four reagent bottles with different filling volumes.
Figure 5:
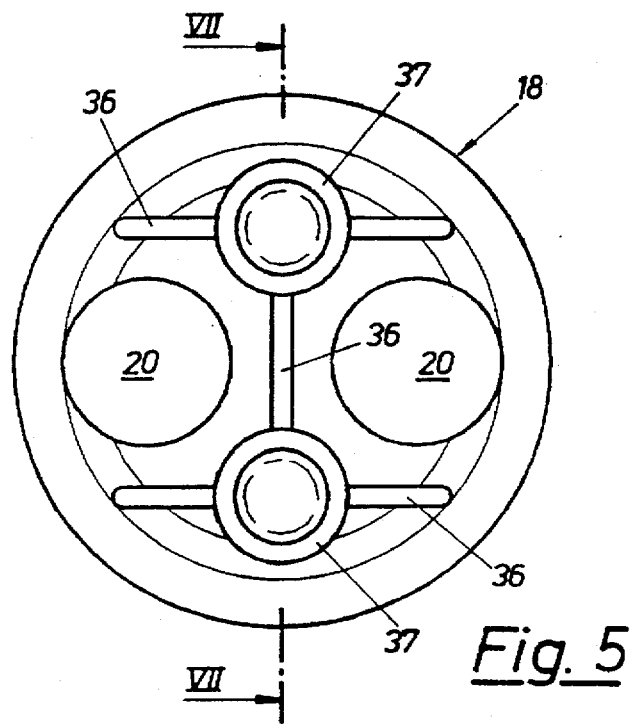
Figure 7:
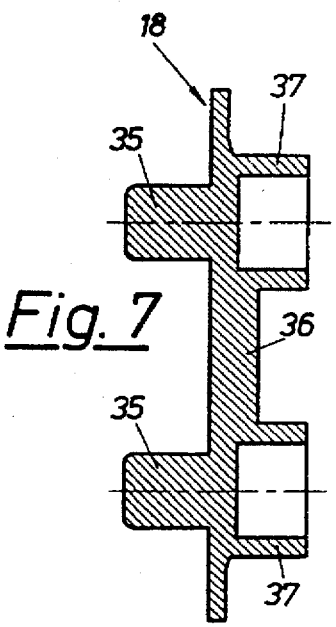

FIG. 5 shows a view from above of the supporting plate 18 following arrow in FIG. 4, and FIG. 6 shows a section according to FIG. 4, and FIG. 7 a section along line VII—VII in FIG. On one side the supporting plate 18 has cylindrical projections 35 which provide anchorage in the elastic stopper 6, on the other side it is reinforced by stiffening ribs 36. For better handling in the filling plant, the supporting plate is further provided with guide elements 37.

If optical methods are employed for level measuring, for example, if a light-guiding rod 10' is used that is suitable for insertion, it will be an advantage for the neck 4' of the sample discharge opening to exhibit an enlargement 21 taking up air bubbles which enter the reagent bottle 1 during insertion of the light-guiding rod and could interfere with the optical measuring process. Any air bubbles can thus rise and collect in the enlargement 21.

As is seen in FIG. 3, the reagent bottle 1 has a recessed grip 24 on either side 22, 23, which will reduce the cross-section of the bottle in the recessed area and increase the stability of the reagent bottle 1.

Empty reagent bottles may be reused as waste containers in the sample analyzer 3, as is shown in FIG. 2. The empty reagent bottle is removed from the analyzer and the elastic stopper seals up again by elastic deformation in areas 16. The reagent bottle may then be inserted into a receiving part 25 of the analyzer 3, during which process the elastic stopper 6 in the sample discharge openings 4 is pierced by a connecting line 26 leading to a vacuum pump. To ensure stability of the reagent bottle even at a slight vacuum, a depression 27 is provided on either side 22, 23 approximately in the middle, the two recesses 27 stabilizing the two sides 22, 23, relative to each other. Before the reagent bottle 1 is used as a waste container, a sealing element 28 is inserted into the air inlet 5. When the waste bottle is docked onto a spring-loaded cover 34 of the analyzer, a unit 29 is inserted into the air inlet 5 which comprises a feed line 30 for the liquid and gaseous media in the analyzer, and an element 31 for level measuring. This element may also be configured as a light-guiding rod.

As a rule, an analyzer contains several reagent and waste bottles simultaneously, which have different capacities. FIGS. 8 to 11 show various sizes of bottles, i.e., a 25 ml bottle is presented in FIG. 8, a 100 ml bottle in FIG. 9, a 500 ml bottle in FIG. 10, and an 800 ml bottle in FIG. 11. The largest bottle of this set, the 800 ml bottle of FIG. 8, may be used as a waste container upon drainage. The reagent bottles of FIGS. 8 to 11 have an annular groove 32 (FIG. 8) running along the outside of the neck 4', of the sample discharge opening 4, or two opposite dents 33 used for holding the reagent bottles in a filling plant.

We claim:

1. reagent bottle which is insertable into a sample analyzer, said reagent bottle comprising a hollow body which provides a first side that defines both a sample discharge opening and an air inlet opening, said sample discharge opening and said air inlet opening respectively defining axes which are parallel to each other, both said sample discharge opening and said air inlet opening docking onto air inlet sampling elements of said sample analyzer when said reagent bottle is inserted into said sample analyzer; an elastic, pierceable stopper which is sealingly positioned in said discharge opening to define an external side facing away from said body and an internal side which faces an interior of said body; and a protective foil which covers said external side of said stopper; said stopper defining a first recess in said external side to provide a first puncturing site where said sampling element of said analyzer can puncture said foil, and a first prepunctured, tightly and elastically closed sealing area which extends in a direction between said first recess and said interior of said body.

2. Reagent bottle according to claim 1, wherein said stopper defines a second recess in said external side thereof to provide a second puncturing site where an element for measuring a level of media contained in the interior of said body when said bottle is inserted in the sample analyzer can puncture said foil, and a second prepunctured, tightly and elastically closed sealing area which extend in a direction between said second recess and said interior of said body.

3. Reagent bottle according to claim 2, wherein said stopper defines conical sealing faces on said internal side which adjoin said first and second prepunctured sealing areas.

4. Reagent-bottle according to claim 2, wherein said body provides an internal projection and wherein said bottle includes a supporting plate positioned between said internal side of said stopper and said internal projection, said supporting plate providing openings aligned with said first and second recesses.

5. Reagent bottle according to claim 4, wherein said element for measuring a level of media contained in the interior of said body includes a light-guiding-rod, and wherein said body defines an enlarged neck above said sample discharge opening, when said bottle is inserted in said sample analyzer, to receive air bubbles which would otherwise interfere with optical measurements.

6. Reagent bottle according to claim 2, wherein said element for measuring a level of media contained in the interior of said body includes a light-guiding rod, and wherein said body defines an enlarged neck above said sample discharge opening, when said bottle is inserted in said sample analyzer, to receive air bubbles which would otherwise interfere with optical measurements.

7. Reagent bottle according to claim 1, wherein said body provides second opposite sides, at least one of said second sides defining a recessed grip whist reduces a cross-section of said body and increases stability of said reagent bottle.

8. Reagent bottle according to claim 7, wherein said body provides second opposite sides that define generally centrally located depressions in order to stabilize said opposite second sides.

9. Reagent bottle according to claim 1, wherein said body provides second opposite sides that define generally centrally located depressions in order to stabilize said opposite second sides.

10. Reagent bottle according to claim 9, wherein said two depressions are located adjacent each said recessed grip.

11. Reagent bottle according to claim 1, wherein said body defines a neck around said sample discharge opening, said neck including a continuous annular groove in an outer surface thereof for the purpose of holding said reagent bottle in a filling plant.

12. Reagent bottle according to claim 1, wherein said body defines a neck around said sample discharge opening, said neck including-two opposite indents in an outer-surface thereof for the purpose of holding said reagent bottle in a filling plant.

13. Reagent bottle according to claim 1, wherein said first prepunctured, tightly and elastically closed sealing area is an elongated passageway of sufficiently small diameter to be sealingly-closed by elastic material forming said elastic, pierceable stopper.

14. A combination of a sample analyzer and a reagent bottle; said sample analyzer including an air inlet element and a sample inlet element; and said reagent bottle comprising a hollow body which provides a first side that defines both a sample discharge opening and an air inlet opening, said sample discharge opening and said air inlet opening respectively defining axes which are parallel to each other, both said sample discharge opening and said air inlet opening docking onto said air inlet and sampling elements of said sample analyzer when said reagent bottle is inserted into said sample analyzer; an elastic, pierceable stopper which is sealingly positioned in said discharge opening to define an external aide facing away from said body and an internal side which faces a interior of said body; and a protective foil which-covers said external side of said stopper; said-stopper defining a first recess in said external aide to provide a first puncturing site where said sampling element of said analyzer can puncture said foil, and a first prepunctured, tightly and elastically closed sealing area which extends in a direction between said first recess and said interior of said body.

15. A combination of a sample analyzer and a reagent bottle, said sample analyzer including an-air inlet element, a sampling element, a receiving element with connecting line connected to a vacuum pump, and a feeding unit with media feed line and media level measuring element; and said reagent bottle comprising a hollow body which provides a first side that defines both a sample discharge opening and an air inlet opening, said sample discharge opening and said air inlet-opening respectively defining axes which are parallel to each other, both said sample discharge opening and said air inlet opening docking onto said air inlet and sampling elements of said sample analyzer when said reagent bottle is inserted into said sample analyzer; an elastic, pierceable stopper which is sealingly positioned in said discharge opening to define an external side facing away from said body and an internal side which faces an interior of said body; and a protective foil which covers said external side of said stopper; said stopper defining a first recess in said external side to provide a first puncturing site where said sampling element of said analyzer can puncture said foil, and a first prepunctured, tightly and elastically closed sealing area which extends in a direction between said first recess and said interior of said body; said reagent bottle being connectable to said sample-analyzer such that said connecting line thereof extends through said elastic stopper and said feed line and said media level measuring element thereof extend through said air inlet opening.

* * * * *